United States Patent
Bruna et al.

(10) Patent No.: US 6,398,074 B1
(45) Date of Patent: Jun. 4, 2002

(54) RESERVOIR, RESERVOIR FILLING METHOD AND DEVICE FOR DISPENSING FLUID CONTAINED IN THE RESERVOIR

(75) Inventors: Pascal Bruna, Rouen; Jean-Louis Guiffray, Petit Couronne, both of (FR)

(73) Assignee: Valois S.A., Neubourg (FR)

( * ) Notice: Subject to any disclaimer, the term of this patent is extended or adjusted under 35 U.S.C. 154(b) by 0 days.

(21) Appl. No.: 09/623,674

(22) PCT Filed: Mar. 9, 1999

(86) PCT No.: PCT/FR99/00519
§ 371 (c)(1),
(2), (4) Date: Nov. 29, 2000

(87) PCT Pub. No.: WO99/46055
PCT Pub. Date: Sep. 16, 1999

(30) Foreign Application Priority Data

Mar. 10, 1998 (FR) .............................................. 98 02876
Jun. 24, 1998 (FR) .............................................. 98 08017

(51) Int. Cl.⁷ ................................................. B67D 5/00
(52) U.S. Cl. ......................... 222/82; 222/209; 222/386; 222/402
(58) Field of Search ........................... 222/82, 83, 83.5, 222/189.06, 209, 386, 402

(56) References Cited

U.S. PATENT DOCUMENTS

| | | | | |
|---|---|---|---|---|
| 3,537,605 A | * | 11/1970 | Soloway | ..................... 222/386 |
| 4,966,312 A | * | 10/1990 | Waring | ........................ 222/209 |
| 5,368,201 A | * | 11/1994 | Fuchs | .......................... 222/386 |
| 5,511,698 A | * | 4/1996 | Solignac | ..................... 222/386 |
| 5,813,570 A | * | 9/1998 | Fuchs et al. | .................. 222/82 |
| 5,893,484 A | * | 4/1999 | Fuchs et al. | .................. 222/83 |
| 6,257,457 B1 | * | 7/2001 | Oechsel | ....................... 222/386 |

FOREIGN PATENT DOCUMENTS

| | | |
|---|---|---|
| CH | 358 898 | 1/1962 |
| CH | 518 744 | 2/1972 |
| EP | 407 276 | 1/1991 |
| EP | 575 239 | 12/1993 |
| EP | 799 646 | 10/1997 |
| WO | WO 91/12895 | 9/1991 |
| WO | WO 93/11818 | 6/1993 |

\* cited by examiner

Primary Examiner—Joseph A. Kaufman
(74) Attorney, Agent, or Firm—Sughrue Mion, PLLC

(57) ABSTRACT

This invention relates to a reservoir (10) for a fluid product containing a single dose, the reservoir (10) comprising an air inlet (11) and a product outlet (15), the air inlet (11) comprising a product retention device (12 and/or 13) to keep the product in the reservoir (10) until dispensation of the product, and the product outlet (15) being blocked, preferably in a sealed fashion, by a closing ball (16) which is removed from its blocking position by the flow of air when the product is being dispensed. This invention also relates to the method of filling the reservoir and a dispensing device for the product contained in the reservoir using an air blast (20).

19 Claims, 5 Drawing Sheets

Figure 5:
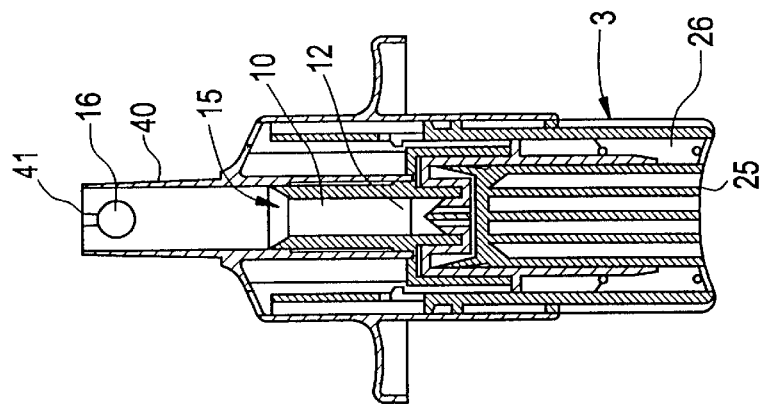

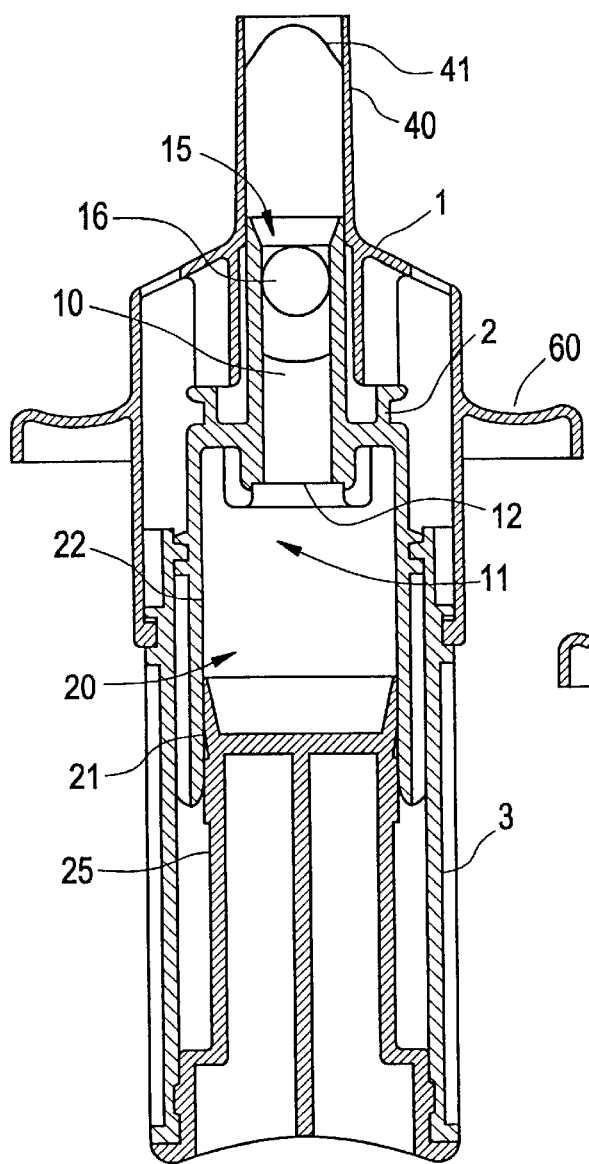
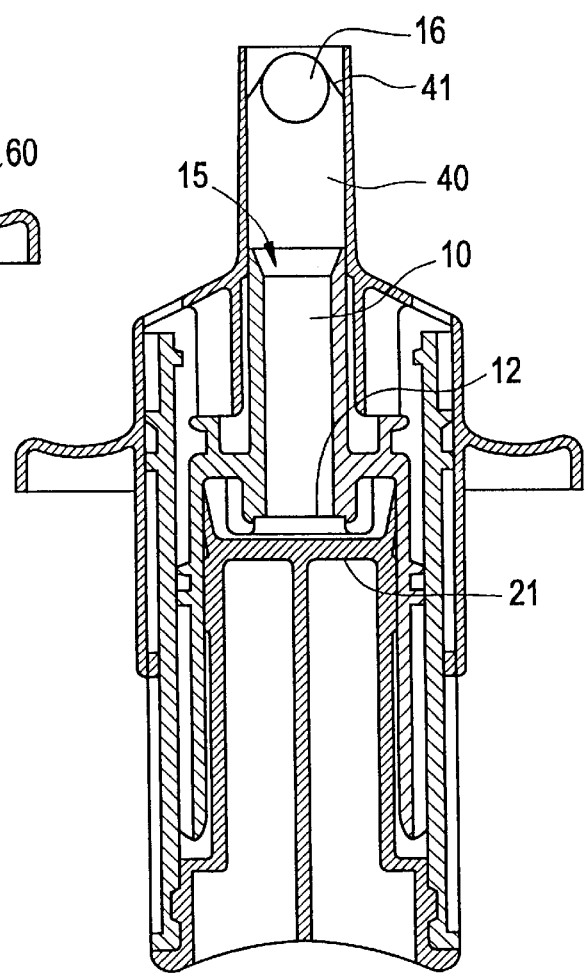

FIG. 9A    FIG. 9B    FIG. 9C
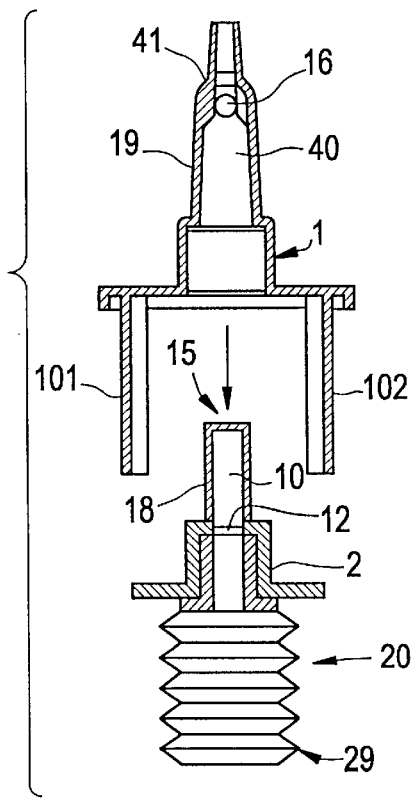
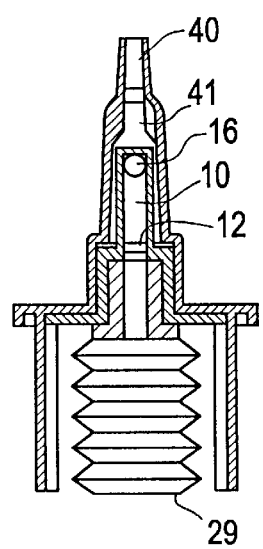
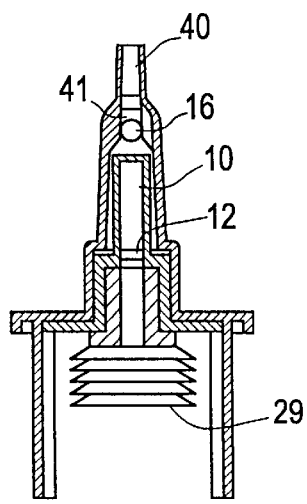
FIG. 10
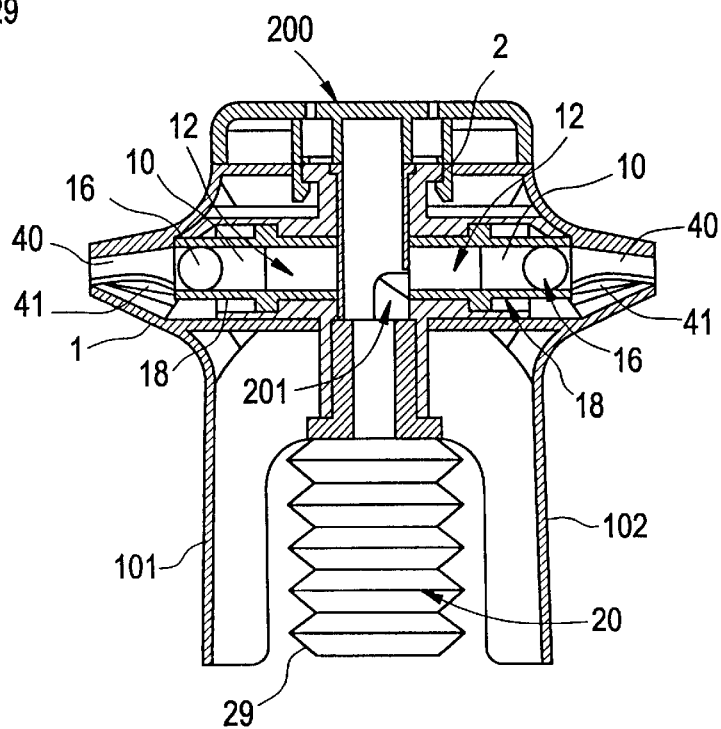

RESERVOIR, RESERVOIR FILLING METHOD AND DEVICE FOR DISPENSING FLUID CONTAINED IN THE RESERVOIR

This invention relates to a reservoir for a fluid or powder product, a method of filling this reservoir, and a device for dispensing, as a single unit, a dose of powder contained in this reservoir using a flow of compressed air.

Expressed in another way, the invention relates more specifically to a device comprising one or more separate, pre-dosed reservoirs, each containing a single dose of product. When there is only one reservoir, the device is a mono-dose device. However the invention is equally applicable to multi-dose type devices, for example two dose or four dose devices, comprising several pre-dosed reservoirs, which allow, notably, a balancing of doses given to both nostrils in the case of nasal application.

Similarly, although the invention can be used with fluid or powder products, it is more particularly applicable to the dispensation of doses of powder and in what follows, reference will be made to this type of product. In effect, the field of powdered products to be dispensed by inhalation, in particular medication based on dry powder, is being developed more and more since dry powder formulations offer numerous advantages compared with liquid suspensions or liquid solutions. They are notably more stable and require neither a solvent nor a preserving agent.

Document EP-0 404 276 discloses a dispenser for a powder or a fluid product which comprises a product reservoir and a gas chamber, in this case the gas being air, and a plunger that can be displaced relative to the reservoir. The reservoir includes an inlet orifice and an outlet orifice, the inlet orifice being blocked by a membrane which separates the reservoir from the gas chamber. Hence, when the device is actuated, the plunger is displaced in the gas chamber, which compresses the air downstream from the membrane until a perforating member integral with the plunger pierces said membrane which allows the flow of air under pressure to pass through the product chamber from its inlet orifice to its outlet orifice carrying a dose of product with it. The main disadvantage of this device is that the outlet orifice from the reservoir is only protected by the detachable cap that the user removes before actuating the device. Hence, between removing the detachable cap and actuating the device, there is a risk of contaminating the product and/or losing the product in the event of handling the device in the wrong way.

In order to resolve this problem, dispensation devices have been proposed in which the outlet orifice from the reservoir is also blocked by a membrane. Hence, when the device is not being used, the inlet and the outlet orifices are blocked in a sealed fashion and the product contained in the reservoir does not risk being contaminated or lost. It is only at the time that the product is being dispensed that the inlet and outlet orifices are unblocked allowing passage of the flow of air which carries the dose of product to the outside of the device. This type of dispenser finds particular application in the field of dispensation of pharmaceutical products in the form of powder, notably by nasal administration. Such a device is notably disclosed in document WO 93/11818.

A problem which does occur with this type of device relates to the piercing of the membrane which blocks the outlet orifice from the reservoir. In effect, it frequently happens that the membrane does not completely unblock the outlet orifice from the reservoir which means that the product can remain built up inside the reservoir on those parts of the membrane that are at the level of the outlet orifice. The result is that not all of the dose of product is dispensed, which particularly in the case of medical treatment is not generally acceptable since a precise and total administration of the dose contained in the reservoir is often a condition for the effectiveness of the treatment.

One aim of this invention is to provide a reservoir for a fluid or powder product and a dispensing device which does not have the disadvantages mentioned above.

A particular aim of this invention is to provide a device for the dispensing of a fluid or powder product which ensures complete and precise dispensation of the dose of product contained in the reservoir.

Another aim of this invention is to provide a device for dispensation of a fluid or powder product which ensures a finely sprayed administration of the dose of product contained in the reservoir.

Another aim of this invention is to provide a reservoir for a fluid or powder product and a dispensation device which are simple and inexpensive to manufacture and to assemble.

A further aim of this invention is to provide a reservoir for a fluid or powder product and a dispensation device that prevents any risk of contamination of the dose of product before its administration to the user of the device.

Another aim of this invention is to provide a device for the dispensation of a fluid or powder product which can be used several times with different pre-dosed reservoirs.

Another aim of this invention is to provide a method of filling such a reservoir which is the most simple and economic possible.

Therefore the subject of this invention is a reservoir for a fluid or powder product containing a single dose of product, the reservoir comprising an air inlet and a product outlet, said air inlet comprising a product retention device to keep the product in the reservoir until dispensation of the product, said product outlet being blocked, preferably in sealed fashion, by a closing ball which is removed from its blocking position by an air flow created at the time of dispensation of the product.

Preferably the device for retaining the product is permeable to air.

Advantageously, the product is a powder and the powder retaining device is a grid, the openings of which have dimensions less than the particle size of the powder.

Advantageously, the air inlet of the reservoir is blocked by a closing membrane that forms a seal to both product and air.

Preferably, downstream from said membrane in the direction of the air flow, the reservoir comprises said grid permeable to the air and which does not allow passage of the powder, in order to retain the powder in the reservoir after the closing membrane has been opened.

Preferably, said ball is removed from its blocking position when a minimum pre-determined pressure is created in the reservoir by said air blast.

According to one preferred embodiment, the reservoir comprises a cylindrical sleeve to receive the dose of powder, said sleeve incorporating said air inlet opening and said product outlet opening, a cylindrical cowl being fixed in a sealed manner around said cylindrical sleeve, said cowl being open on the side of the product outlet and including means of fixing the ball in order to keep said ball fixed before its placement in its blocking position in the sleeve and after its removal by the flow of air.

Advantageously, said cowl fixing means for the ball comprise fins arranged on the inside wall of the cowl, so that after its removal from its blocking position, the ball is held fixed in the cowl in a centered fashion so that an optimum discharge of air/powder mixture can flow around it.

Another subject of this invention is a device for the dispensation of a fluid or powder product that comprises an air blast to generate an air flow when the device is actuated and at least one reservoir.

Preferably the air blast comprises a piston closing, preferably in a sealed manner, and sliding within a chamber connected to said reservoir air inlet, said piston being connected to an actuating member, actuated by the user.

As a variant, the air blast comprises a bellows connected to said reservoir air inlet.

Preferably, the reservoir product outlet is connected, preferably in a sealed manner, to an outlet channel, the diameter of which is greater than the diameter of the ball, said channel comprising means of stopping the ball to prevent its expulsion out of the device at the time the product is being expelled.

Preferably, the reservoir air inlet is blocked by a closing membrane that forms a seal to both product and air, the device comprising means of opening the reservoir air inlet designed to open said membrane before the expulsion of the dose of product.

Advantageously, said means of opening the reservoir air inlet comprise a piercing needle fitted to pierce said closing membrane and to connect said reservoir to said air blast.

According to one particular embodiment of the invention, said air blast comprises resetting means of the kind that enables the device to be recharged and/or reused.

Advantageously, the resetting means comprises a spring that returns the piston and the actuating member to their respective stand-by positions.

Advantageously, said reservoir is mounted in a detachable manner in said device in such a way that it can be replaced after each actuation of the device.

It is possible that, before its actuation, the whole of the device is packaged in air-tight packaging.

Another objective of this invention is a method of filling such a powder reservoir, comprising the steps of:
  introducing a dose of powder into the sleeve, through the product outlet opening
  fitting the cowl around the sleeve, said cowl including the closing ball held fixed by said ball fixing means
  inserting the ball into the product outlet opening of the sleeve.

Figure 4:
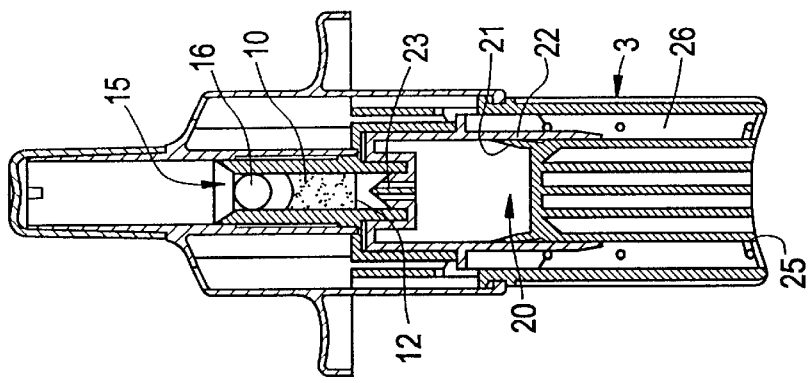
Figure 3:
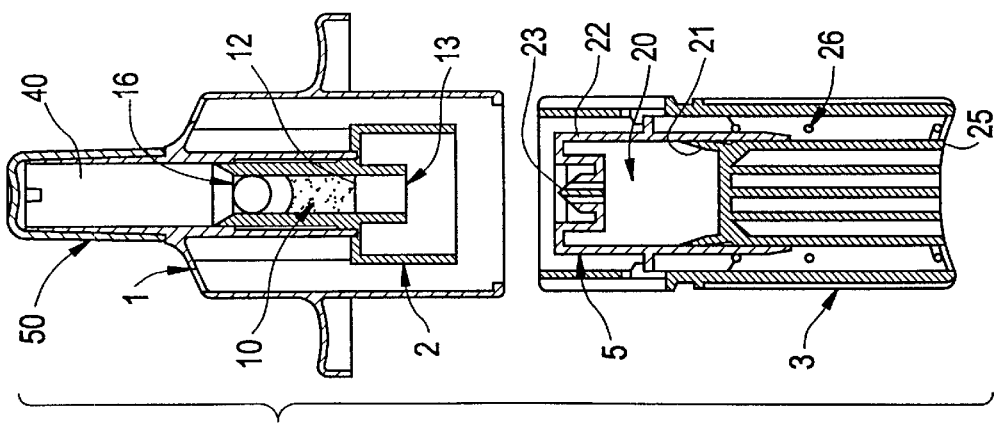
Figure 6:
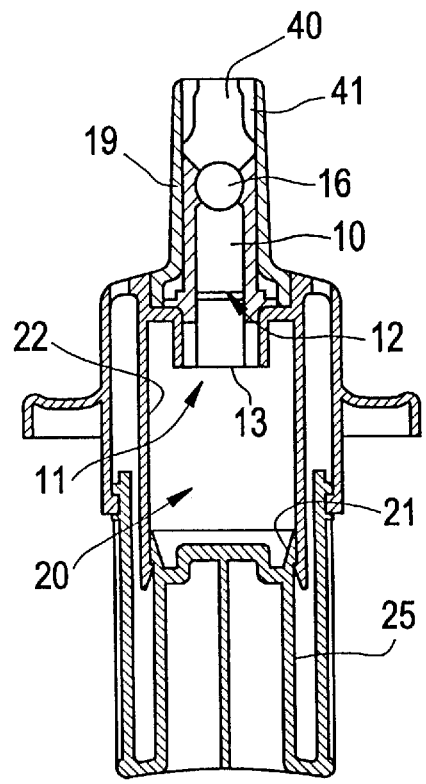
Figure 7:
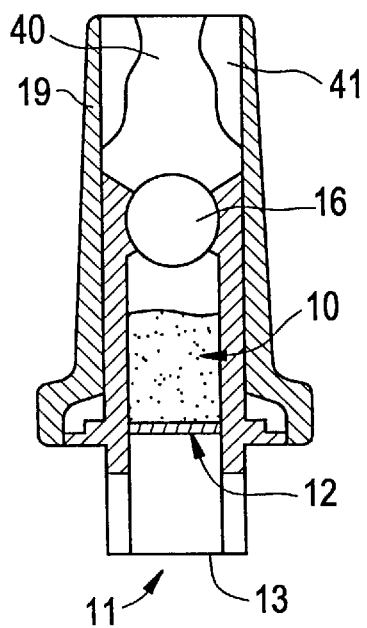
Figure 8D:
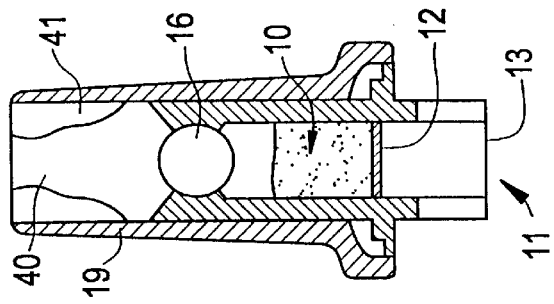
Figure 8C:
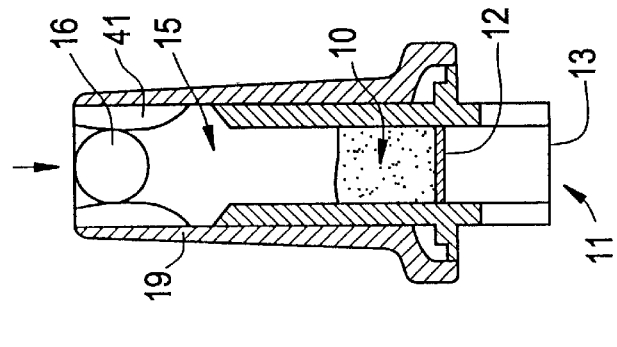
Figure 8B:
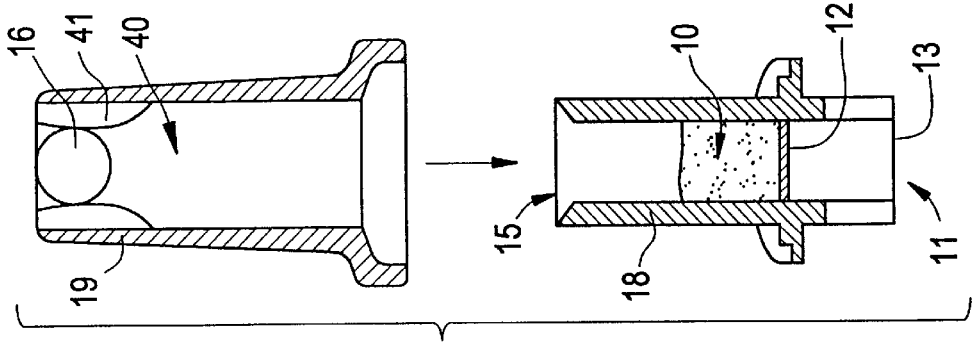
Figure 8A:
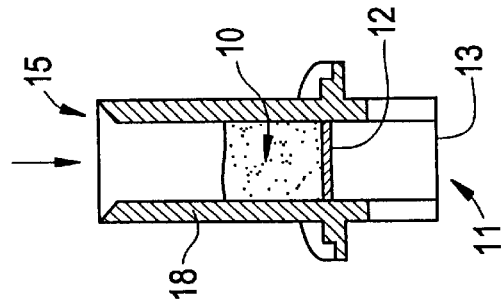

Other characteristics and advantages of this invention will more clearly become apparent during the detailed description that follows of several embodiments of this invention, given by way of non-limitative examples with respect to the attached drawings in which:

FIG. 1 is a diagrammatic sectional view of a first embodiment of this invention, before actuation, FIG. 2 is a view similar to that in FIG. 1, after actuation, FIG. 3 is a diagrammatic sectional view of a second embodiment of this invention, before actuation, FIG. 4 is a view similar to that in FIG. 3, after actuation, FIG. 5 is a view similar to that in FIGS. 3 and 4, after expulsion of the product FIG. 6 is a diagrammatic sectional view of a third embodiment of this invention, FIG. 7 is a diagrammatic sectional view of a reservoir according to an advantageous embodiment of the invention, FIGS. 8a to 8d show the steps of the filling method according to the invention, FIGS. 9a, 9b and 9c represent a fourth embodiment of the invention, respectively before assembly, before actuation and after actuation, and FIG. 10 represents a fifth embodiment of the invention.

Referring to FIGS. 1 and 2, a first embodiment of the invention is shown. The device comprises an upper body 1 incorporating an outlet channel 40 and gripping means 60 allowing the user to actuate the device. Inside this upper body 1 an element is mounted, designated in its assembly by reference number 2, that incorporates the reservoir 10 and the air chamber 22 for the air blast 20. It is possible for this element 2 to be produced in one piece with the body 1. A lower body 3 is also provided in order to be able to slide relative to the upper body 1 and relative to the element 2, the user exerting a push force on the lower body to actuate the device.

In the example represented in FIGS. 1 and 2, reservoir 10 and the air chamber 22 are integral with said element 2 and a piston 21 integral with the lower body 3 is arranged in such a way that it blocks and can slide within said air chamber 22, preferably in sealed fashion. The piston 21 can be integral with an actuating member 25, called a plunger below, fixed to the lower body 3, as shown in the drawings, but it could also be produced in one piece with the lower body 3, in which case the latter acts as the actuating member.

The reservoir according to the invention comprises an air inlet 11 and a product outlet 15. The air inlet 11 comprises a member for retaining the product 12 intended to keep the product in the reservoir until the device is actuated. This product retaining member 12 is preferably produced in the form of a grid permeable to air, the openings of which are of dimensions which are less than the size of the particles of powder, if the product is a powder, or of dimensions sufficiently small to retain a fluid product inside the reservoir by capillary action. Advantageously, and as is shown in the drawings, the air inlet to the reservoir 10 is directly connected to the air blast 20, preferably in a sealed fashion, in such a way that all of the flow of air under pressure that will be created when the device is actuated will flow from the air inlet 11 through the entire reservoir 10 to the product outlet 15 in order to expel the dose contained in the reservoir.

The product outlet 15 from the reservoir 10 is, according to the invention, blocked by a closing ball 16, or more generally by a closing element 16 of spherical shape, which is designed to be removed from its blocking position shown in FIG. 1 by said flow of air which is created by the actuation of the device as will be explained below.

Hence, when the user actuates the device, he exerts a pressure on the plunger 25 in such a way that the piston 21 compresses the air contained in the chamber 22 of the air blast 20. The grid 12 being permeable to air, the compression of the air in chamber 22 will be transmitted to the reservoir 10 and consequently will be applied to the closing ball 16 which is blocking the product outlet 15. The dimensions of the closing ball 16 and its fixing at the reservoir product outlet 15 are such that the ball 16 is removed from its blocking position shown in FIG. 1, when a minimum predetermined pressure is created through the reservoir 10 in said air blast 20. Hence, when this minimum pressure is reached, the ball is suddenly moved towards the outlet channel 40 of the device and the flow of air created by the air blast 20 expels all of the dose contained in the reservoir 10. The pre-compression created by this closing ball 16 ensures that when it is removed from its blocking position, the energy accumulated in the hand of the user is such that the piston 21 integral with the plunger 25 is propelled within the chamber 22 thereby creating a powerful air flow, that is to say an air flow suitable to finely spray the dose of product and notably to get rid of any product agglomerates if it is a powder product. The flow of air is therefore total, that is to say that the whole of the volume of air contained in chamber 22 is expelled in the form of a flow of air when the device is actuated. All of the characteristics relating to the dispensation of the dose, such as the volume of the dose, the volume and the rate of flow of the air are therefore predetermined in a precise manner and are therefore exactly reproducible. Effectiveness is therefore guaranteed.

Preferably, the outlet channel 40 has a diameter greater than the diameter of the closing ball 16 in order to allow the dose of product to be expelled through the outlet channel 40 by flowing around the ball 16. Preferably, the channel 40 comprises means 41 of arresting or fixing the ball 16 in order to prevent its expulsion out of the device when the product is being expelled.

The use of a ball 16, or more generally a spherical element to close the powder outlet 15 from the reservoir 10 allows one to guarantee total release of the product from this product outlet during expulsion in such a way that the disadvantage that exists with membranes is avoided. Furthermore, the spherical shape ensures good flow of the product dose around the closing element 16 when this is in the outlet channel 40. Hence, the invention allows one to ensure the effective dispensation of the entire dose contained in the reservoir 10 without risk of partial retention of product in the dispensation device.

Preferably, the ball 16 closes off the outlet orifice 15 from the reservoir 10 in a sealed manner, and this outlet orifice is connected in a sealed manner with the outlet channel 40. Similarly, the reservoir air inlet is preferably connected in a sealed manner to the air chamber 22 of the air blast 20, and the piston 21 closes off said air chamber 22 preferably in a sealed manner. In this way, before actuation of the device, the product contained inside the reservoir is completely separated in a sealed manner from the atmosphere. Nevertheless, it may be considered that this hermetic seal of the product contained in the reservoir 10 be reinforced before use of the device by packaging the entire device inside airtight packaging (not shown) which will be removed by the user just before using the device.

In FIGS. 3 to 5, a second embodiment of this invention is shown. Items identical or similar to those in the first embodiment have been given the same reference numbers. The main difference in this second embodiment is that, at the reservoir 10 air inlet, a tearable closing membrane 13 has been provided that forms a seal to both product and air. In order to open this closing membrane 13, the device includes means 23 of opening the reservoir 10 air inlet which are designed to open said membrane 13 before expulsion of the dose of product.

This sealed closing membrane 13 can be used as the product retention device 12. Preferably, as shown in FIGS. 3 to 5, the reservoir 10 comprises in addition to the closing membrane 13, a product retention device, such as the grid 12 described with reference to the first embodiment. The advantage in this case is that after opening the closing membrane 13 with opening means 23, there is no risk that the product flows into the inside of the air chamber 22 of the air blast 20. Advantageously, said means of opening the air inlet comprise a piercing needle 23 which is suitable for piercing said closing membrane 13 at the same time connecting the reservoir 10 to the air blast 20. In the example shown in FIGS. 3 to 5, the piercing needle 23 includes grooves or bores that allow this connection to be made.

In the embodiment shown in FIGS. 3 to 5, the air blast, in particular the air chamber 22 is no longer integral with the reservoir 10, and the whole device is made in two parts, an upper part comprising the upper body 1 and the element 2 incorporating the reservoir 10, and the lower part comprising the lower body 3 and a second element 5 creating the air chamber 22 and incorporating at its end, said piercing needle 23. The first step when the user wishes to actuate the device is to assemble the two parts of the device, as shown in FIG. 4. During this assembly, the piercing needle 23 advantageously pierces the membrane 13 which is closing the air inlet of the reservoir 10. The linkage between the parts can be created in any fashion but notably by clicking on to one another. Preferably the link between the second element 5 which incorporates the air chamber 22 and the first element 2 which incorporates the reservoir 10 is made in a sealed fashion at the time the two parts of the device are assembled. When the device is in its configuration shown in FIG. 4, the expulsion of the dose of product is carried out in the same way as in the case of the first embodiment, that is to say, the user presses on the plunger 25 thereby compressing the air contained in the air chamber 22 by means of the piston 21, said pressure, when it reaches the minimum threshold required, removing the closing ball 16 from its blocking position and allowing the dose to be expelled by the air flow.

As shown in the drawings, the plunger 25 and the piston 21 can be produced as one piece, such as an actuating cylinder 25 including the piston 21 at its end. Similarly, the outlet orifice of the outlet channel 40 can be closed off by a detachable cap 50, as shown in FIGS. 3 and 4. It is of course understood that the closing cap 50 can be fitted onto the device in FIGS. 1 and 2 and that it could be omitted in the second embodiment if this were also to be packaged in an air-tight manner in suitable packaging (not shown).

According to a variant of the invention, the device can be produced in a reusable version, that is to say it can be reused several times with different pre-dosed reservoirs 10. In this case, the device can include right from the start, several reservoirs which are emptied successively during successive actuations of the device. This is the case for a multi-dose device. With regard to mono-dose devices, they can be designed to be rechargeable. To do this, the reservoir 10 is mounted in a detachable manner in the body 1, in such a way that it can be easily replaced after each actuation of the device. In addition, the air blast includes resetting means 26, in particular, a spring, which is fitted to return the piston 21, the plunger 25 and therefore also the lower body 3 to their respective stand-by positions. Referring to FIGS. 3 to 5, element 2 which incorporates the reservoir 10 is force fitted into the upper body 1 and, after use of the device it can be easily replaced by a new element 2 which includes an empty reservoir by simple separation of the two parts of the device and replacement of the element 2. It is also possible to consider producing the first embodiment described with reference to FIGS. 1 and 2 in a rechargeable form.

Referring to FIGS. 6 and 7, another advantageous embodiment of the invention is shown, in which the reservoir 10 according to the invention comprises a tubular sleeve 18 that receives the powder, said sleeve incorporating said air inlet opening 11 and said product outlet opening 15. As may be seen in these Figures, the reservoir 10 of the invention comprises, in addition, a substantially cylindrical cowl 19 fitted or nested around the sleeve 18, said cowl 19 being open at both ends. The part of the cowl 19 which axially goes past the product outlet opening 15 therefore forms a part of the expulsion channel 40 of the product. This cowl 19 can be mounted in a sealed fashion on the sleeve 18 in a fixed or detachable way in any suitable manner, the assembly of these two pieces of the reservoir having to be sufficiently rigid to resist the actuation of the dispensation device.

The air inlet 11 of the reservoir 10 preferably includes a grid 12 and a membrane 13 as described previously. This sealed closing membrane 13 can serve as a retaining device 12 for the product since it retains the powder in the reservoir. Preferably, the reservoir 10 includes the closing membrane 13 and the grid 12 described above. The advantage in this case is that after the opening of the closing membrane 13 by the opening means there is no risk whatsoever that the powder will run into the inside of the air blast.

The part of the cowl 19 forming an outlet channel 40 has a diameter greater than the diameter of the closing ball 16 to allow the dose of product to be expelled by flowing around the ball 16. According to the invention, the cowl 19 comprises fixing means 41 for the ball 16 to prevent the expulsion of the ball out of the device when the product is being expelled and to keep it fixed before and after its placing in its blocking position. These means of fixing a ball are advantageously produced in the form of several fins 41 distributed around the internal periphery of said cowl 19, and fitted to trap the ball 16 in a central position in the expulsion channel 40.

Hence, during the expulsion of the powder/air mixture, the mixture can flow around the ball and thereby form a clean, straight and even jet.

In the case of the detachable fitting of the cowl 19 onto the sleeve 18, the fixing of the ball 16 in the cowl 19 after the expulsion of the product allows one to eliminate the risk of loss of the ball during separation of the cowl 19 and the sleeve 18.

These means 41 of fixing the ball also provide another advantage which will be explained below with reference to the method of filling the reservoir.

In effect, the design of the reservoir of the invention according to the embodiment in FIGS. 6 and 7 allow its filling and assembly to be simplified from which a cost reduction results.

The successive steps of the method of filling the reservoir 10 are represented in FIGS. 8a to 8d.

First, a precise dose of product is introduced into the sleeve 18, as represented by the arrow A in FIG. 1a. The powder is retained in the sleeve 18 by a grid 12.

Next, the unit formed by the cowl 19 and the ball 16 trapped in the ball fixing means 41 of the cowl, is fitted around the sleeve 18. This step is represented by the arrow B in FIG. 1b. Advantageously, the cowl 19 and the sleeve 18 include respective stop means in order to define the assembled position of the reservoir.

Then, the ball 16 is inserted into the opening of the product outlet 15 of the sleeve 18, along arrow C in FIG. 1c, in order to block the reservoir.

Advantageously, the air inlet 11 is blocked in a sealed manner by the membrane 13, and the ball 16 blocks the outlet of the reservoir also in a sealed manner in such a way that after step C above, the contents of the reservoir are totally isolated from the exterior of the reservoir.

The main advantages of the method according to the invention are:

assembly of the reservoir is limited to mounting the two parts, namely nesting the cowl/ball unit onto the sleeve. The assembly machine for the reservoir is therefore simplified: this simplification is made possible by the presence of means 41 of fixing the ball in the cowl 19;

insertion of the ball into the sleeve 18 is facilitated because it is already positioned close to the outlet opening 15 and in a centered way, during the fitting of the cowl 19.

Using the reservoir according to the invention with the cowl 19 fitted around the sleeve 18 blocked by the ball 16 therefore provides the double advantage of simplifying the method of filling and assembling the reservoir and of ensuring the total and perfect dispensation of the dose of powder contained in the reservoir.

In FIGS. 9a, 9b and 9c another embodiment of the invention is shown in which the air blast 20 of the dispensation device is produced using a bellows 29 actuated by the user. The operation of such a bellows 29 to create a flow of air is well known and will therefore not be more fully described here. Advantageously, the upper body 1 comprises two lateral uprights 101, 102 which in the assembled state of the device surround the bellows 29 to prevent accidental actuation, while allowing the user to press on the bottom of the bellows 29 to actuate the device and expel a dose. The filling method described in relation to FIGS. 8a to 8d is applicable here, as may be seen in FIGS. 9a and 9b.

Referring to FIG. 10, another embodiment of the invention is shown in which the dispensation device is a multi-dose device in particular a two dose device. Hence the device includes two reservoirs 10 produced according to the invention, and which in the example shown are, arranged horizontally each being connected to its respective outlet channel. The device includes a rotating device 200 which controls a flow selector 201 fitted to direct the air flow created by the air blast 20 (here the bellows 29) towards the reservoir 10 chosen by the user according to the position of said rotating device 200. This type of device can, of course, include more than two reservoirs and the positioning of them can also be created in a different manner to that represented in FIG. 10.

Other variants and modifications are possible without departing from the context of this invention, and the invention is not limited to embodiment examples described in the drawings. In particular, the embodiments described above can be combined with one another and the various characteristics are not limited to the particular embodiments for which they have been described. On the other hand, one can consider using a gas other than air to create the gas flow under pressure.

What is claimed is:

1. A reservoir (10) for a product containing a single dose of product, the reservoir (10) comprising an air inlet (11) and a product outlet (15), said air inlet (11) comprising a product retention device (12 and/or 13) to keep the powder in the reservoir until dispensation of the powder and said powder outlet (15) being closed, preferably in a sealed manner, by a closing ball (16) which is removed from its closing position by a flow of air created at the time the powder is being dispensed.

2. A reservoir according to claim 1, in which the powder retention device (12) is permeable to air.

3. A reservoir according to claim 2, in which the powder retention device is a grid (12) the openings of which have dimensions smaller than the particle size of the powder.

4. A reservoir according to claim 1, in which the air inlet (11) of the reservoir (10) is closed by a closing membrane (13) that forms a seal to both powder and air.

5. A reservoir according to claim 3, in which the reservoir (10) comprises downstream from a membrane (13), in the direction of the flow of the air, said grid (12) which is permeable to air and which forms a seal to the powder, in order to retain the powder in the reservoir (10) after opening the closing membrane (13).

6. A reservoir according to claim 1 in which said ball (16) is removed from its closing position when a minimum predetermined pressure is created in the reservoir (10) by said flow of air.

7. A reservoir according to claim 1 in which the reservoir (10) comprises a cylindrical sleeve (18) to receive the dose of powder, said sleeve (18) incorporating said air inlet opening (11) and said product outlet opening (15), a cylindrical cowl (19) being fitted in a sealed fashion around the cylindrical sleeve (18), said cowl (19) being open on the product outlet side (15) and comprising means for fixing the ball (41) in order to keep said ball fixed (16) before its placement in its closing position in the sleeve (18) and after its removal by the flow of air.

8. A reservoir according to claim 7, in which said ball fixing means (41) of the cowl (19) comprise fins (41) arranged on the internal wall of the cowl, in such a way that after its removal from its closing position, the ball (16) is held fixed in the cowl in a centered fashion, allowing optimum flow of the air/powder mixture around it.

9. A device for dispensing a fluid or powder product, characterized in that it comprises an air blast (20) to generate an air flow at the time the device is actuated and at least one reservoir (10) according to claim 1.

10. A device according to claim 9, in which the air blast (20) comprises a piston (21) blocking, preferably in a sealed fashion, and sliding within a chamber (22) connected to said air inlet (11) of the reservoir (10), said piston (21) being connected to an actuating member (25) actuated by the user.

11. A device according to claim 9, in which the air blast (20) comprises a bellows (29) connected to said air inlet (11) of the reservoir (10).

12. A device according to claim 9 in which the product outlet (15) from the reservoir (10) is connected, preferably in a sealed fashion, to an outlet channel (40) the diameter of which is greater than the diameter of the ball (16), said channel (40) comprising stop means (41) for the ball (16) to prevent its expulsion out of the device when the product is being expelled.

13. A device according to claim 9 in which the air inlet (11) of the reservoir (10) is closed by a closing membrane (13) that forms a seal to both the powder and the air, the device comprising means (23) of opening the reservoir air inlet (11) suitable for opening said membrane (13) before expulsion of the dose of product.

14. A device according to claim 13, in which said means (23) of opening the reservoir air inlet (11) comprise a piercing needle (23) suitable for piercing said closing membrane (13) and for connecting said reservoir (10) to said air blast (20).

15. A device according to claim 9 in which said air blast (20) comprises resetting means (26) such that the device can be recharged and/or reused.

16. A device according to claim 10, in which the resetting means comprise a spring (26) that returns the piston (21) and the actuating member (25) to their respective stand-by positions.

17. A device according to claim 9 in which said reservoir (10) is mounted in a detachable manner in said device in such a way that it can be replaced after each actuation of the device.

18. A device according to claim 9 in which before actuation, the whole of the device is packaged in an air-tight package.

19. A method of filling a powder reservoir according to claim 7, characterized in that it comprises the steps of:

introducing (A) a dose of powder into the sleeve (18), through the product outlet opening (15), fitting (B) the cowl (19) around the sleeve (18), said cowl (19) comprising the closing ball (16) kept fixed by said ball fixing means (41), inserting (C) the ball (16) in the product outlet opening (15) of the sleeve (18).

* * * * *